US00PP07969P

United States Patent [19]

Hanes

[11] Patent Number: Plant 7,969

[45] Date of Patent: Sep. 8, 1992

[54] GERANIUM NAMED ECLIPSE SALMON ORANGE

[75] Inventor: Mitchell Hanes, Morgan Hill, Calif.

[73] Assignee: Goldsmith Seeds, Inc., Gilroy, Calif.

[21] Appl. No.: 666,887

[22] Filed: Mar. 8, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

[57] ABSTRACT

A new Geranium variety particularly distinguished by its vigorous, fast-rooting growth and its large semi-double salmon orange flowers which are borne in large umbels carried by strong tall stalks well above dark green foliage.

1 Drawing Sheet

BACKGROUND OF THE NEW PLANT

The present invention comprises a new and distinct cultivar of Geranium, botanically known as *Pelargonium hortorum* Bailey, and hereinafter referred to by the cultivar name Eclipse Salmon Orange. The new cultivar is a hybrid seedling resulting from a controlled crossing of an orange flowered dark leaf seed parent and an orange flower pollen parent selected from our collection of plants maintained at our nursery at Gilroy, Calif. for breeding purposes.

This new cultivar is a product of a planned breeding program intended to create new Geranium cultivars with salmon orange colored flowers, semi-double flower form, dark green foliage, vigorous growth and superior cutting productivity.

The new cultivar was developed in 1988 at the Company nursery at Gilroy, Calif. and has been repeatedly asexually reproduced by cuttings in Gilroy, Calif. and in Guatemala over a two year period. It has also been trialed at Okemos, Mich. and in each case it has been found to retain its distinctive characteristics through successive generations and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true to that herein specified as can be reasonably obtained by conventional photographic procedures.

DESCRIPTION OF THE NEW CULTIVAR

The following detailed descriptions set forth the distinctive characteristics of this new Geranium plant. The data which defines these characteristics were collected from asexual reproductions carried out by Goldsmith Seeds, Inc. in Gilroy, Calif., the plant history having been taken on 30 week old plants, blossomed under natural light in a greenhouse and color readings were taken in the greenhouse at Gilroy, on May 29, 1990 at 2:00 p.m. under ambient light. Color references are primarily to The R.H.S. Colour Chart of The Royal Horticultural Society of London, England.

THE PLANT

Classification:

*Botanical.*—*Pelargonium hortorum* Bailey.

*Commercial.*—Zonal geranium.

Form: Semi-Dwarf.

Height: 11 to 14 cm., as a 5½ inch potted plant, excluding blooms.

Growth: Vigorous and upright.

Strength: Strong, fast-rooting plant with dark green foliage that has good shipping ability as rooted or unrooted cuttings.

Foliage: Abundant quantity.

Leaves:

*Size.*—Diameter about 5.5 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 2.5 to 4.5 cm. long.

*Color.*—Upper side: Dark green with a darker green zone on the outer half of the leaf. Underside: Lighter green color without zonation. Ribs and veins not prominently different from upper surface.

*Petioles.*—About 4 to 6 cm. in length.

THE BUD

Size:

*Diameter.*—About 7 mm.

*Length.*—About 1.8 cm. to 2.0 cm. at time of bud opening.

Shape: Pointed ovoid.

Color: When sepals first divide, RHS 43-C.

Sepals: Five or six in number, flat behind petals.

*Shape.*—Pointed linear lanceolate in form.

*Color.*—Green RHS 144-A, with purple streaks in an open flower.

THE FLOWER

Blooming habit: Continuous throughout the year.

Size: Approximately 4.5 cm. diameter, 1.1 cm. deep, irregularly radially symmetrical.

Form: Cup-shaped when bloom first opens, later flattening to an irregular shape with maturity.

Petals: Six to seven imbricate outer petals, 1.4–1.8 cm. wide and approximately 2 cm. long. 5 to 6 inner smaller petaloids of varying shape. Both the outer petals and inner petaloids are salmon orange (RHS 43-B). Veins are the same color as the interveinal regions. Color changing little with age. Underside of petals lighter. Petals and petaloids soft and satiny.

Pedicel: Approximately 2.5–3 cm. in length.

Persistence: Nonshattering flower.

INFLORESCENSE

Type: An umbel composed of approximately 30 flowers, erect or laterally ascending.

Peduncle: Approximately 8–9.5 cm. in length. Green acquiring a reddish tint with age.

REPRODUCTIVE ORGANS

Stamens:

*Anthers.*—Seven to nine positioned below the mature stigma, dull red prior to anthesis.

*Filaments.*—White near base and mid length, graduating to dull red near anther.

*Pollen.*—Orange in color.

Pistil:

*Number.*—One.

*Length.*—Approximately 8 mm.

*Style.*—Length: About 4 mm. Color: Purplish red.

*Stigma.*—Five or six linear lobes of near equal length, curling back toward ovary, purplish-red.

Ovaries: At anthesis, densely pubscent with white hairs, oblong and green, drying to a light brown at maturity.

Fruit: Partially fertile.

I claim:

1. A new and distinct cultivar of Geranium plant substantially as herein shown and described characterized by dark green foliage with faint zonation, salmon orange flower color, and semi-double flowers on large umbels, the plant being fast-rooting and having a vigorous bush-like growth habit.

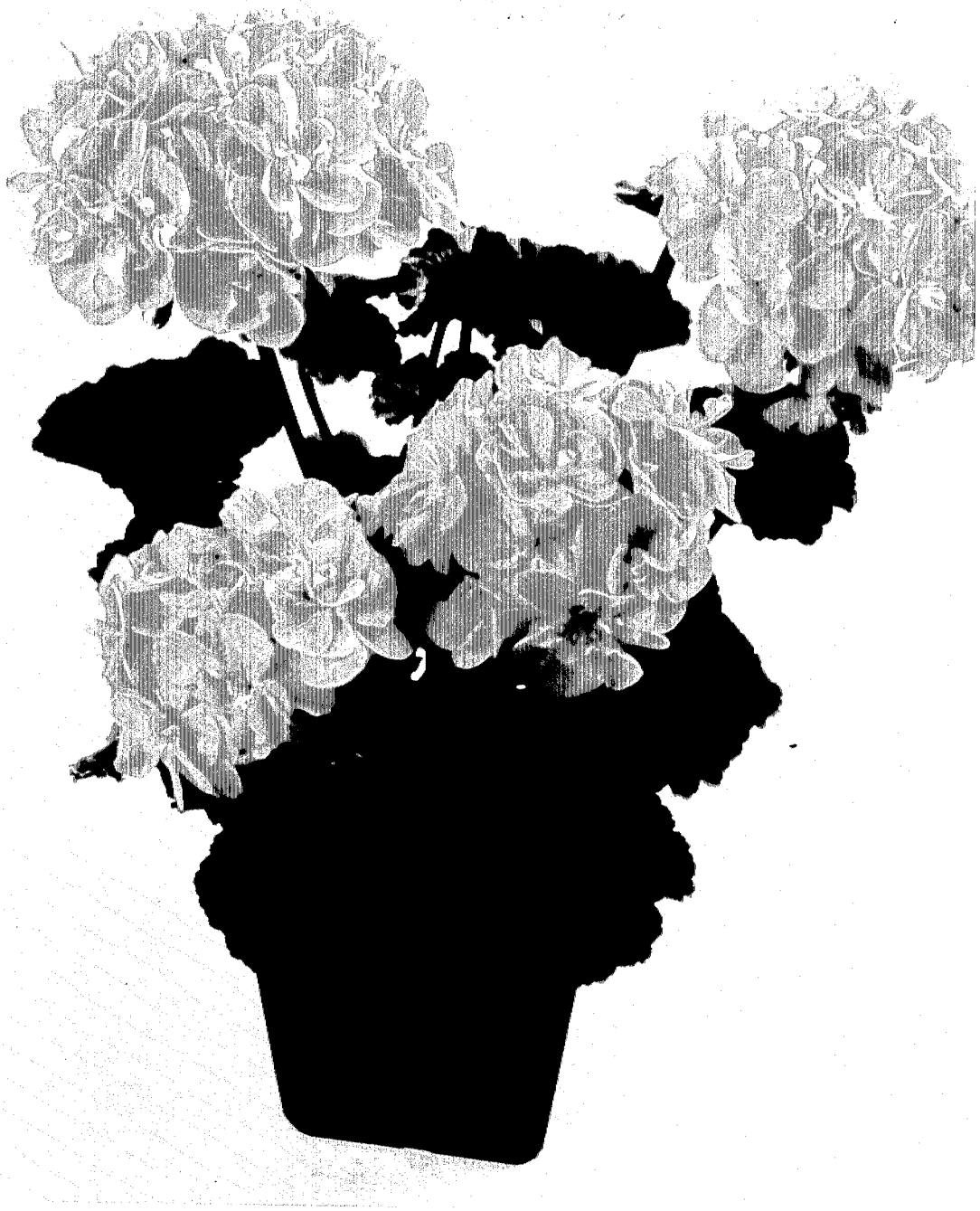

* * * * *